United States Patent
Himeda et al.

(10) Patent No.: US 10,315,190 B2
(45) Date of Patent: Jun. 11, 2019

(54) CATALYST USED FOR DEHYDROGENATION OF FORMIC ACID, METHOD FOR DEHYDROGENATING FORMIC ACID, AND METHOD FOR PRODUCING HYDROGEN

(71) Applicant: National Institute of Advanced Industrial Science and Technology, Tokyo (JP)

(72) Inventors: Yuichiro Himeda, Ibaraki (JP); Wan-Hui Wang, Ibaraki (JP); Yuichi Manaka, Ibaraki (JP); Yuki Amamoto, Ibaraki (JP)

(73) Assignee: National Institute of Advanced Industrial Science and Technology, Chiyoda-ku, Tokyo (JP)

( * ) Notice: Subject to any disclaimer, the term of this patent is extended or adjusted under 35 U.S.C. 154(b) by 0 days.

(21) Appl. No.: 15/027,943

(22) PCT Filed: Oct. 8, 2014

(86) PCT No.: PCT/JP2014/076953
§ 371 (c)(1),
(2) Date: Apr. 7, 2016

(87) PCT Pub. No.: WO2015/053317
PCT Pub. Date: Apr. 16, 2015

(65) Prior Publication Data
US 2016/0250626 A1    Sep. 1, 2016

(30) Foreign Application Priority Data
Oct. 11, 2013    (JP) .................................. 2013-213576

(51) Int. Cl.
*B01J 31/22* (2006.01)
*C07F 15/00* (2006.01)
(Continued)

(52) U.S. Cl.
CPC ......... *B01J 31/2295* (2013.01); *B01J 31/183* (2013.01); *B01J 31/1815* (2013.01);
(Continued)

(58) Field of Classification Search
CPC .................................................... B01J 31/2295
See application file for complete search history.

(56) References Cited

U.S. PATENT DOCUMENTS

2010/0034733 A1*   2/2010   Fukuzumi ............ B01J 31/1815
                                                    423/658.2
2010/0068131 A1    3/2010   Laurenczy
(Continued)

FOREIGN PATENT DOCUMENTS

EP    2543675    1/2013
JP    3968431    6/2007
(Continued)

OTHER PUBLICATIONS

Photochemical production of hydrogen and carbon dioxide from formate using mixed-ligand iridum complexes as catalyst Karen J. Watson Inorganica Chimica Acta, vol. 197, pp. 125-127 (Year: 1992).*
(Continued)

*Primary Examiner* — Douglas B Call
(74) *Attorney, Agent, or Firm* — Carmody Torrance Sandak & Hennessey LLP

(57) ABSTRACT

A catalyst including, as effective ingredient, complex represented by Formula (1) which contains bidentate ligand including aromatic heterocyclic 5-membered ring having 2 or more nitrogen atoms, or represented by Formula (2) which contains bidentate ligand including: aromatic heterocyclic 5-membered ring having 2 or more nitrogen atoms; and 6-membered ring having 1 or more nitrogen atoms, isomer or salt of the complex:

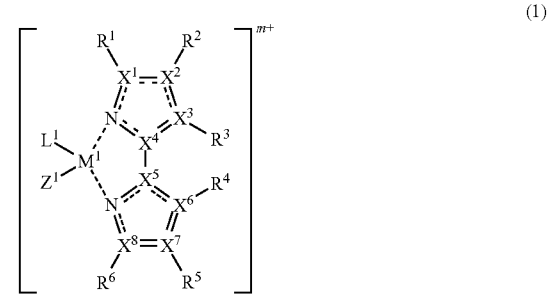

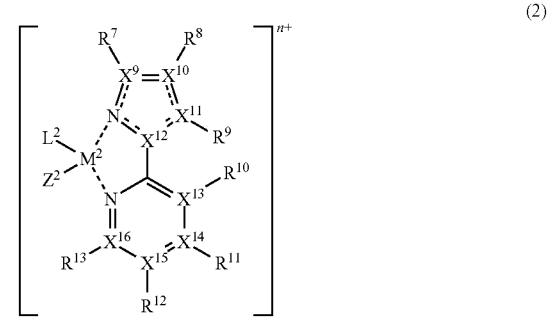

where
  $M^1$ and $M^2$ denote transition metal such as iridium;
  $X^1$ to $X^{16}$ each independently denote nitrogen or carbon;
  $R^1$ to $R^{13}$ denote, for example, hydrogen atom, alkyl group, or hydroxy group, provided that when $X^i$ (where i denotes 13 to 16) is nitrogen, $R^i$ is absent at position corresponding to the nitrogen;
(Continued)

$L^1$ and $L^2$ denote, for example, an aromatic anionic ligand;

$Z^1$ and $Z^2$ denote any ligand or are absent; and m and n denote positive integer, 0, or negative integer.

5 Claims, 2 Drawing Sheets

(51) Int. Cl.

| | | |
|---|---|---|
| *C01B 3/22* | (2006.01) | |
| *H01M 8/0612* | (2016.01) | |
| *C01B 3/26* | (2006.01) | |
| *B01J 31/18* | (2006.01) | |
| *C01B 32/50* | (2017.01) | |

(52) U.S. Cl.
CPC .................. *B01J 31/22* (2013.01); *C01B 3/22* (2013.01); *C01B 3/26* (2013.01); *C01B 32/50* (2017.08); *C07F 15/0033* (2013.01); *C07F 15/0073* (2013.01); *H01M 8/0612* (2013.01); *B01J 2231/763* (2013.01); *B01J 2531/822* (2013.01); *B01J 2531/827* (2013.01); *B01J 2531/96* (2013.01); *B01J 2540/10* (2013.01); *C01B 2203/0277* (2013.01); *C01B 2203/066* (2013.01); *C01B 2203/1064* (2013.01); *H01M 8/0618* (2013.01)

(56) References Cited

U.S. PATENT DOCUMENTS

| | | |
|---|---|---|
| 2012/0321550 A1 | 12/2012 | Fukuzumi |
| 2013/0220825 A1 | 8/2013 | Joya |
| 2013/0244865 A1 | 9/2013 | Muranaka |
| 2014/0299817 A1 | 10/2014 | Hull |
| 2015/0166337 A1 | 6/2015 | Himeda |
| 2016/0121318 A1* | 5/2016 | Goldberg ............. B01J 31/1815 560/265 |

FOREIGN PATENT DOCUMENTS

| | | |
|---|---|---|
| JP | 4009728 | 9/2007 |
| JP | 2010083730 | 4/2010 |
| JP | 2010208927 | 9/2010 |
| JP | 4572393 | 11/2010 |
| JP | 4875576 | 2/2011 |
| JP | 4822253 | 9/2011 |
| JP | 5030175 | 7/2012 |
| JP | 2013193983 | 9/2013 |
| WO | 2008047312 | 4/2008 |
| WO | 2011108730 | 9/2011 |
| WO | 2012070620 | 5/2012 |
| WO | 2013040013 | 3/2013 |
| WO | 2013111860 | 8/2013 |
| WO | WO 2014/130714 * | 8/2014 |

OTHER PUBLICATIONS

Schaub, et al., "A Process for the Synthesis of Formic Acid by CO2 Hydrogenation: Thermodynamic Aspects and the Role of CO," Agnew. Chem. Int. Ed., vol. 50, pp. 7278-7282 (2011).

Boddien et al., "CO2-"Neutral" Hydrogen Storage Based on Bicarbonates and Formates," Agnew. Chem. Int. Ed., vol. 50, pp. 6411-6414 (2011).

Tanaka, et al., "Mechanistic Studies on the Reversible Hydrogenation of Carbon Dioxide Catalyzed by an Ir-PNP Complex," Organometallics, vol. 30, pp. 6742-6750 (2011).

Boddien, et al., "Efficient Dehydrogenation of Formic Acid Using an Iron Catalyst," Science, vol. 33, pp. 1733-1736 (Sep. 23, 2011).

Loges, et al., "Controlled Generation of Hydrogen from Formic Acid Amine Adducts at Room Temperature and Application in H2/O2 Fuel Cells," Agnew. Chem. Int. Ed., vol. 47, pp. 3962-3965 (2008).

Zell, et al., "Efficient Hydrogen Liberation from Formic Acid Catalyzed by a Well-Defined Iron Pincer Complex Under Mild Conditions," Chem. Eur. J., vol. 19, pp. 8068-8072 (2013).

Barnard, et al., "Long-Range Metal-Ligand Bifunctional Catalysis: Cyclometallated Iridium Catalysts for the Mild and Rapid Dehydrogenation of Formic Acid," Royal Society of Chemistry, vol. 4, pp. 1234-1244 (2013).

Sponholz, et al., "Towards a Practical Setup for Hydrogen Production from Formic Acid," ChemSusChem Communications, vol. 6, pp. 1172-1176 (2013).

Fellay, et al., "A Viable Hydrogen-Storage System Based on Selective Formic Acid Decomposition with a Ruthenium Catalyst," Agnew Chem. Int. Ed., vol. 47, pp. 3966-3968 (2008).

Papp, et al., "A Charge/Discharge Device for Chemical Hydrogen Storage and Generation," Agnew Chem. Int. Ed., vol. 50, pp. 10433-10435 (2011).

Fukuzumi, et al., "Unusually Large Tunneling Effect on Highly Efficient Generation of Hydrogen and Hydrogen Isotopes in pH-Selective Decomposition of Formic Acid Catalyzed by a Heterodinuclear Iridium-Ruthenium Complex in Water," J. Am. Chem. Soc., vol. 132, pp. 1496-1497 (2010).

Maenaka et al., "Catalytic Interconversion Between Hydrogen and Formic Acid at Ambient Temperature and Pressure," Energy Environ. Sci., vol. 5, pp. 7360-7367 (2012).

Himeda et al., "Transfer of Hydrogenation of a Variety of Ketones Catalyzed by Rhodium Complexes in Aqueous Solution and Their Application to Asymmetric Reduction Using Chiral Schiff Based Ligands," Journal of Molecular Catalysis A: Chemical., vol. 195, pp. 95-100 (2003).

Himeda, et al., "Half-Sandwich Complexes with 4,7-Dihydroxy-1,10-phenanthroline: Water Soluble, Highly Efficient Catalysts for Hydrogenation of Bicarbonate Atributable to the Generation of an Oxyanion on the Catalyst Ligand," Organometallics, vol. 23, pp. 1480-1483 (2004).

Himeda, Y., "Conversion of CO2 into Formate by Homogeneously Catalyzed Hydrogenation in Water: Tuning Catalytic Activity and Water Solubility Through the Acid-Base Equilibrium of the Ligand," Eur. J. Inorg. Chem., pp. 3927-3941 (2007).

Himeda, et al., "Simultaneous Tuning of Activity and Water Solubility of Complex Catalysts by Acid-Base Equilibrium of Ligands for Conversion of Carbon Dioxide," Organometallics, vol. 26, pp. 702-712 (2007).

Himeda, et al., "Catalytic (transfer) Deuterogenation in D20 as Deuterium Source with H2 and HCO2H as Electron Sources," Royal Society of Chemistry, pp. 6286-6288 (2009).

Himeda, Y., "Highly Efficient Hydrogen Evolution by Decomposition of Formic Acid Using an Iridium Catalyst with 4,4'—dihydrogen-2,2'-bipyridine," Green Chemistry, vol. 11, pp. 2018-2022 (2009).

Himeda, et al. "Interconversion Between Formic Acid and H2/CO2 Using Rhodium and Ruthenium Catalysts for CO2 Fixation and H2 Storage," ChemSusChem, vol. 4, pp. 487-493 (2011).

Hull, et al., Reversible Hydrogen Storage Using CO2 and a Proton-Switchable Iridium Catalyst in Aqueous Media Under Mild Temperatures and Pressures, Nature Chemistry, vol. 4, pp. 383-388 (May 2012).

Wang, et al., "Highly Efficient D2 Generation by Dehydrogenation of Formic Acid in D20 Through H+/D+ Exchange on an Iridium Catalyst: Application to the Synthesis of Deuterated Compounds by Transfer Deuterogenation," Chem. Eur. J., vol. 18, pp. 9397-9404 (2012).

Muller, et al., "Structure-Reactivity Relationships in the Hydrogenation of Carbon Dioxide with Ruthenium Complexes Bearing Pyridinylazolato Ligands," Chem. Eur. J., vol. 19, pp. 7825-7834 (2013).

Ziessel, et al., "Synthesis and Molecular Structure of New Families of Iridium(III)-Cp and Rhodium(III)-Cp Complexes Derived from 1,2-Dicyanoethene-1,2-dithiolate, 2,2'-biimidazole or 2,2'-bithiazole. Single Crystal Structures of [(n5-Me5C5)Ir(biimH2)CI]CI and [(n5-Me5C5)Rh(dcdt)]," Journal of Organometallic Chemistry, vol. 441, pp. 143-143 (1992).

(56) References Cited

OTHER PUBLICATIONS

Prasad, et al., "Mono and Dinuclear Half-Sandwich Platinum Group Metal Complexes Bearing Pyrazolyl-Pyrimidine Ligands: Synthesis and Structural Studies," Journal of Organometallic Chemistry, vol. 695, pp. 495-504 (2010).

Himeda, Y., "Highly Efficient Hydrogen Evolution by Decomposition of Formic Acid Using an Iridium Catalyst with 4,4'- dihydroxy-2,2'-bipyridine," Green Chem., vol. 11, pp. 2018-2022 (2009).

Fukuzumi, et al., "Hydrogen Storage and Evolution Catalysed by Metal Hydrogen Complexes," Dalton Transactions, vol. 42, pp. 18-28 (2013).

Manaka, et al., "Efficient H2 Generation from Formic Acid Using Azole Complexes in Water," Catalysis Science & Technology, vol. 4, pp. 34-37 (2014).

Soriano et al., "Synthesis and Characterization of Ru(arene) Complexes of Bispyrazolylazines: Catalytic Hydrogen Transfer of Ketones", Inorganica Chimica Acta, Apr. 23, 2009, pp. 4486-4492, vol. 362, No. 12.

Gupta et al., "Ruthenium Half-Sandwich Complexes with Tautomerized Pyrazolyl-pyridazine Ligands: Synthesis, Spectroscopic and Molecular Structural Studies", Journal of Organometallic Chemistry, Jul. 15, 2009, pp. 2618-2627, vol. 694, No. 16.

Gupta et al., "Study of New Mononuclear Platinum Group Metal Complexes Containing η5 and η6-Carbocyclic Ligands and Nitrogen based Derivatives and Formation of Helices due to N-H... Cl Interactions", Journal of Molecular Structure, Aug. 27, 2010, pp. 205-213, vol. 979, No. 1-3.

Venkateswara et al., "Study of Half-Sandwich Mono and Dinuclear Complexes of Platinum Group Metals Containing Pyrazolyl Pyridine Analogues: Synthesis and Spectral Characterization", Journal of Chemical Sciences, May 1, 2012, pp. 565-575, vol. 124, No. 3.

Shavaleev et al., "Steric Hindrance at Metal Centre Quenches Green Phosphorescence of Cationic Iridium(III) Complexes with 1-(2-pyridyl)-pyrazoles", Inorganica Chimica Acta, Mar. 14, 2013, pp. 210-214, vol. 404.

Gomez-De La Torre et al., "Synthesis and Characterization of Palladium(II) Complexes with New Polydentate Nitrogen Ligands. Dynamic Behavior Involving Pd-N. Bond Rupture. X-Ray Molecular Structure of [{Pd(η3-C4H7)}2(Me—BPzTO)](4-MeC6H4SO3)[Me-BPzTO = 4,6-Bis(4-methylpyrazol-1-yl)-1,3,5-triazin-2-olate]", Inorganic Chemistry, Dec. 1, 1998, pp. 6606-6614, vol. 37, No. 26.

Wang et al., "Highly Robust Hydrogen Generation by Bioinspired Ir Complexes for Dehydrogenation of Formic Acid in Water: Experimental and Theoretical Mechanistic Investigations at Different pH", ACS Catalysis, Jul. 30, 2015, pp. 5496-5504, vol. 5, No. 9.

Ziessel, et al., "Synthesis and Molecular Structure of New Families of Iridium(III)-Cp and Rhodium(III)-Cp Complexes Derived from 1,2-Dicyanoethese-1,2-dithiolate, 2,2'biimidazole. Single Crystal Structures of [(n5-Me5C5)Ir(biimH2)Cl]Cl and [(n5—Me5C5)Rh(dcdt)]," Journal of Organometallic Chemistry, vol. 441, pp. 143-154 (1992).

European Search Report, dated Jul. 10, 2017, (17 sheets).

* cited by examiner

CATALYST USED FOR DEHYDROGENATION OF FORMIC ACID, METHOD FOR DEHYDROGENATING FORMIC ACID, AND METHOD FOR PRODUCING HYDROGEN

TECHNICAL FIELD

The present invention relates to a catalyst used for dehydrogenation of formic acid, a method for dehydrogenating formic acid using the catalyst, and a method for producing hydrogen.

BACKGROUND ART

Hydrogen ($H_2$) has been produced in an amount of about five hundred billion $Nm^3$ all over the world. The hydrogen has attracted much attention as future clean energy as well as has been applied for a variety of uses such as refinement of oil or production of ammonia. For example, a fuel cell is capable of efficiently supplying electricity when the hydrogen is supplied externally thereto. However, the hydrogen is highly reactive gas, so that it is difficult to be transported and stored. Therefore, there has been a need for a safe and inexpensive transportation and storage technology in order to stably supply the hydrogen. In the field of the fuel cell, there has been a problem that a poisoning substance is by-produced on a surface of an electrode catalyst by the action of carbon monoxide. Thus, there has been a need to supply high purity hydrogen generally containing 10 ppm or less of carbon monoxide.

As a hydrogen storage method, at present, a method for storing hydrogen as high pressure gas in a gas cylinder is commonly used. However, in this method, there are problems of safety upon transportation of the high pressure gas, and hydrogen brittleness of container materials. A method for storing hydrogen gas in the form of liquid hydrogen under an extremely low temperature is also used. However, there are problems that much energy is consumed in a liquefaction process and that the liquid hydrogen is lost in a percentage of 3% per day to 6% per day due to vaporization.

In order to solve the above described problems with regard to hydrogen transportation and storage technologies, there has been considered a method for storing hydrogen as liquid fuel (e.g., methanol and formic acid) which is obtained by hydrogenating carbon dioxide. For example, formic acid (HCOOH) has recently been attracted the attention as a hydrogen storage material since the formic acid, which is in the liquid form at normal temperature and has a relatively low toxicity, can be reversibly converted to hydrogen ($H_2$) and carbon dioxide ($CO_2$). However, there has been a problem that a dehydrogenation reaction of the formic acid using a conventionally known catalyst generally requires a high temperature of 200° C. or higher, and generates carbon monoxide as a by-product. Therefore, there has been a need to develop a catalyst which allows high quality hydrogen to be produced from the formic acid under a mild condition.

Recently, many reports have been made with regard to a dehydrogenation reaction of formic acid using a metal complex catalyst (PTLs 1 and 2 and NPLs 1 to 8). In these reactions, although hydrogen is produced through dehydrogenation of formic acid, carbon monoxide is hardly by-produced. However, most of them need organic solvents or amine additives. On the other hand, a reaction in water free of organic additives is problematic in low catalytic activity and durability (PTLs 3 to 7, NPLs 9 to 12). Besides the above reports, the present inventors have been found catalysts which are extremely highly active in the dehydrogenation reaction of formic acid in water free of organic additives. However, these catalysts are problematic in durability because they are easily decomposed in a high-concentration formic acid solution or under a high temperature reaction condition (PTLs 8 to 14, NPLs 13 to 21).

CITATION LIST

Patent Literature

PTL 1: International Publication No. WO2008/047312
PTL 2: International Publication No. WO2012/070620
PTL 3: Japanese Patent (JP-B) No. 4572393
PTL 4: JP-B No. 4875576
PTL 5: International. Publication No. WO2011/108730
PTL 6: Japanese Patent Application Laid-Open (JP-A) No. 2010-083730
PTL 7: JP-A No. 2010-208927
PTL 8: JP-B No. 3968431
PTL 9: JP-B No. 4009728
PTL 10: JP-B No. 4822253
PTL 11: JP-B No. 5030175
PTL 12: International. Publication No. WO2013/040013
PTL 13: International Publication No. WO2013/111860
PTL 14: JP-A No. 2013-193983

Non-Patent Literature

NPL 1: Schaub, T.; Paciello, R. A. Angew. Chem.-Int. Edit. 2011, 50, 7278.
NPL 2: Boddien, A.; Gartner, F.; Federsel, C.; Sponholz, P.; Mellmann, D.; Jackstell, H.; Junge, H.; Beller, M. Angew. Chem.-Int. Edit. 2011, 50, 6411.
NPL 3: Tanaka, R.; Ymashita, M.; Chung, L. W.; Morokuma, K.; Nozaki, K. Organometallics 2011, 30, 6742.
NPL 4: Boddien, A.; Mellmann, D.; Gaertner, F.; Jackstell, H.; Junge, H.; Dyson, P. J.; Laurenczy, G.; Ludwig, H.; Beller, M. Science 2011, 333, 1733.
NPL 5: Loges, B.; Boddien, A.; Junge, H.; Beller, M. Angew. Chem.-Int. Edit. 2008, 47, 3962.
NPL 6: Zell, T.; Butschke, B.; Ben-David, Y; Milstein, D. Chem.-Eur. J. 2013, 19, 8068.
NPL 7: Barnard, J. H.; Wang, C.; Berry, N. G.; Xiao, J. Chem. Science 2013, 4, 1234.
NPL 8: Sponholz, P.; Mellmann, D.; Junge, H.; Beller, M. ChemSusChem 2013, 6, 1172.
NPL 9: Fellay, C.; Dyson, P. J.; Laurenczy, C. Angew. Chem.-Int. Edit. 2008, 47, 3966.
NPL 10: Papp, G.; Csorba, J.; Laurenczy, G.; Joo, h. Angew. Chem.-Int. Edit. 2011, 50, 10433.
NPL 11: Fukuzumi, S.; Kobayashi, T.; Suenobu, T. J. Am. Chem. Soc. 2010, 132, 1496.
NPL 12: Maenaka, Y.; Suenobu, T.; Fukuzumi, S. Energy Environ. Sci. 2012, 5, 7360.
NPL 13: Himeda, Y; Onozawa-Kornatsuzaki, N.; Sugihara, H.; Arakawa, Kasuga, K. J. Mol. Catal. A-Chem. 2003, 195, 95
NPL 14: Himeda, Y.; Onozawa-Komatsuzaki, N.; Sugihara, H.; Arakawa, H.; Kasuga, K. Organometallics 2004, 23, 1480.
NPL 15: Himeda, Y. Eur. J. Inorg. Chem. 2007, 3927.
NPL 16: Himeda, Y; Onozawa-Kornatsuzaki, N.; Sugihara, H.; Kasuga, K. Organometallics 2007, 26, 702.
NPL 17: Himeda, Y.; Miyazawa, S.; Onozawa-Komatsuzaki, N.; Hirose, T.; Kasuga, K., Dalton Transactions, 2009, (32), 6286-6288.

NPL 18: Himeda, Y. Green Chem. 2009, 11, 2018.

NPL 19: Himeda, Y.; Miyazawa, S.; Hirose, T. ChemSusChem 2011, 4, 487.

NPL 20: Hull, Jonathan F.; Himeda, Yuichiro; Wang, Wan-Hui; Hashiguchi, Brian; Periana, Roy; Szalda, David J.; Muckerman, James T.; Fujita, Etsuko, Nature Chemistry 2012, 4, 383-388.

NPL 21: Wang, Wan-Hui; Hull, Jonathan F.; Muckerman, James T.; Fujita, Etsuko; Takuji, Hirose; Himeda, Yuichiro, Chemistry—A European Journal 2012, 18, 9397-9404.

SUMMARY OF INVENTION

Technical Problem

The present invention has an object to provide a catalyst allowing hydrogen to be produced through dehydrogenation of formic acid in a highly efficient, highly energy-efficient, highly selectively, and highly durable manner even in a high-concentration aqueous formic acid solution under a high temperature reaction condition.

The present invention also has an object to provide a method for producing hydrogen through dehydrogenation of formic acid using the catalyst in a highly efficient and inexpensive manlier with simple operation, and a method for high-pressure hydrogen free of carbon monoxide so as to stably and continuously supply hydrogen in an amount required for hydrogen consumption devices (e.g., fuel cells).

Solution to Problem

The present inventors conducted extensive studies to solve the above-described problems and consequently have found that a metal complex represented by the following Formula (1) which contains a bidentate ligand including an aromatic heterocyclic 5-membered ring having 2 or more nitrogen atoms or a metal complex represented by the following Formula (2) which contains a bidentate ligand including: an aromatic heterocyclic 5-membered ring having 2 or more nitrogen atoms; and an aromatic heterocyclic 6-membered ring having 1 or more nitrogen atoms is useful for a dehydrogenation reaction of formic acid, to thereby complete the present invention. The present invention includes the following technical means:

[1] A catalyst used for a dehydrogenation reaction of at least one of formic acid and a formic acid salt, the catalyst including:

a complex represented by the following Formula (1) which contains a bidentate ligand including an aromatic heterocyclic 5-membered ring having 2 or more nitrogen atoms, or represented by the following Formula (2) which contains a bidentate ligand including: an aromatic heterocyclic 5-membered ring having 2 or more nitrogen atoms; and a 6-membered ring having 1 or more nitrogen atoms, an isomer or a salt of the complex, as an effective ingredient,

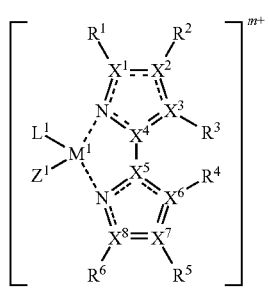

(1)

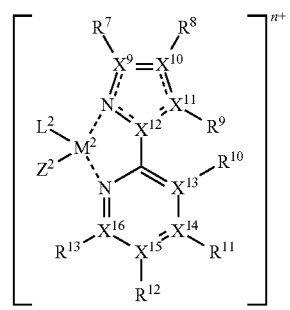

(2)

where $M^1$ and $M^2$ denote a transition metal selected from the group consisting of iridium, rhodium, ruthenium, cobalt, osmium, nickel, iron, palladium and platinum;

$X^1$ to $X^{16}$ each independently denote nitrogen or carbon;

$R^1$ to $R^{13}$ each independently denote a hydrogen atom, an alkyl group, a hydroxy group (—OH), an alkoxy group (—OR), a nitro group, a halogen group, a sulfone group, a carboxylic acid group, an alkylamino group, or a phenyl group, or adjacent R groups may be linked together to form a ring; and $R^1$ to $R^{13}$ may be substituted by one substituent or a plurality of substituents, provided that when $X^i$ (where i denotes 13 to 16) is nitrogen, $R^i$ is absent at a position corresponding to the nitrogen;

$L^1$ and $L^2$ denote an aromatic anionic ligand or an aromatic ligand, and may be substituted by one substituent or a plurality of substituents;

$Z^1$ and $Z^2$ denote any ligand or are absent; and m and n denote a positive integer, 0, or a negative integer.

[2] The catalyst used for a dehydrogenation reaction of at least one of formic acid and a formic acid salt according to [1], wherein $M^1$ or $M^2$ denotes iridium.

[3] The catalyst used for a dehydrogenation reaction of at least one of formic acid and a formic acid salt according to [1] or [2], wherein $L^1$ or $L^2$ denotes a pentamethylcyclopentadienyl ligand.

[4] The catalyst used for a dehydrogenation reaction of at least one of formic acid and a formic acid salt according to any one of [1] to [3], wherein $Z^1$ or $Z^2$ denotes a water molecule, a hydrogen atom, an alkoxide ion, a hydroxide ion, a halide ion, a carbonate ion, a trifluoromethanesulfonate ion, a sulfate ion, a nitrate ion, a formate ion, or an acetate ion, or is absent.

[5] The catalyst used for a dehydrogenation reaction of at least one of formic acid and a formic acid salt according to any one of [1] to [4], wherein the complex has a structure represented by the following Formula (3) or (4):

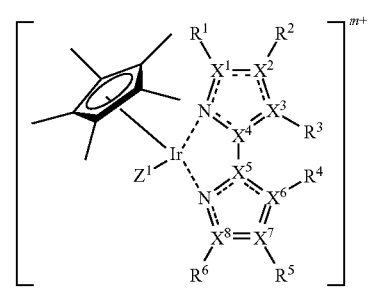

(3)

-continued

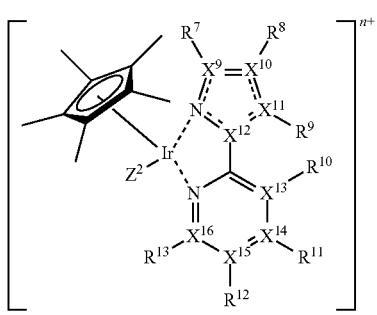
(4)

where

X¹ to X¹⁶, R¹ to R¹³, Z¹, Z², m, and n are the same as defined in the Formula (1) or (2).

[6] The catalyst used for a dehydrogenation reaction of at least one of formic acid and a formic acid salt according to [5], wherein the complex has a structure represented by any selected from the group consisting of the following Formulae (5) to (12):

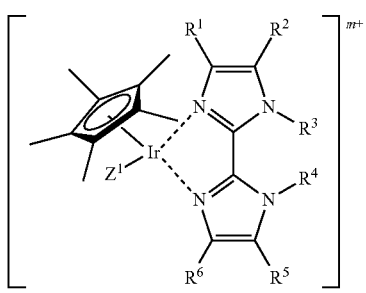
(5)

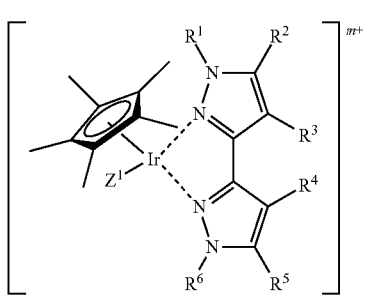
(6)

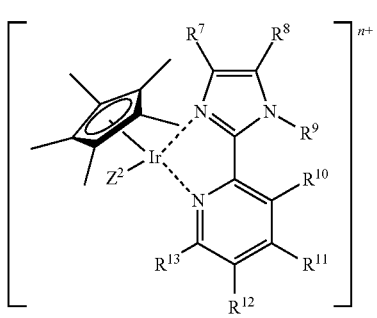
(7)

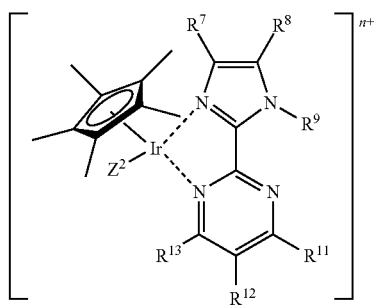
(8)

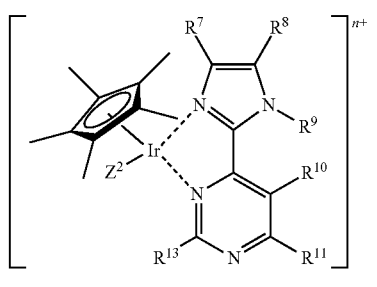
(9)

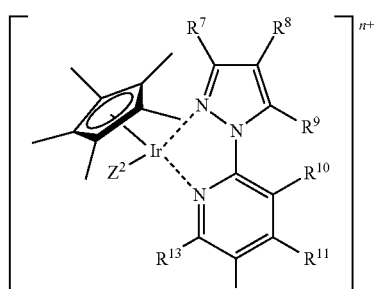
(10)

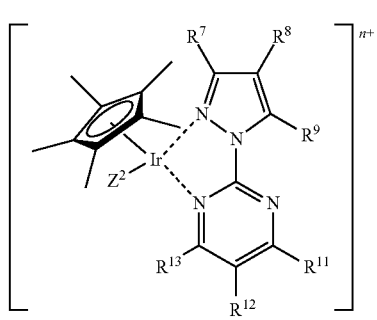
(11)

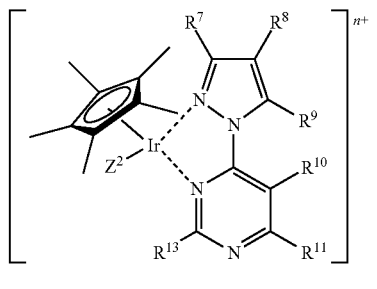
(12)

where

R¹ to R¹³, Z¹, Z², m, and n are the same as defined in the Formula (1) or (2).

[7] The catalyst used for a dehydrogenation reaction of at least one of formic acid and a formic acid salt according to

[6], wherein the complex has a structure represented by any selected from the group consisting of the following Formulae (13) to (21):

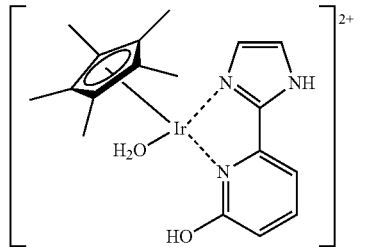
(13)

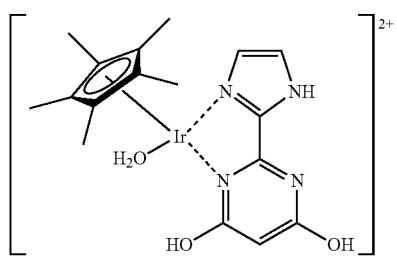
(14)

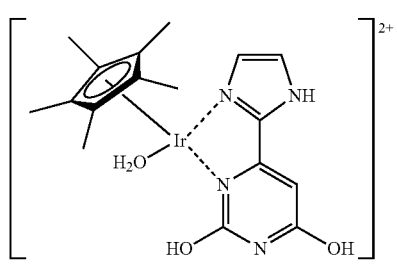
(15)

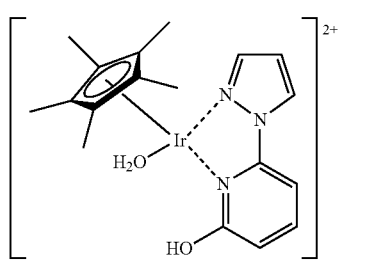
(16)

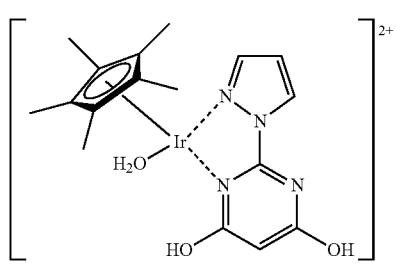
(17)

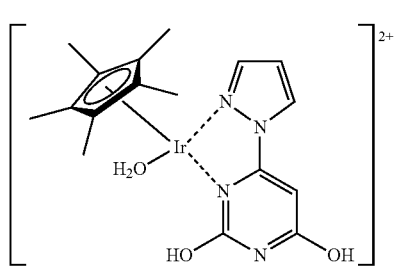
(18)

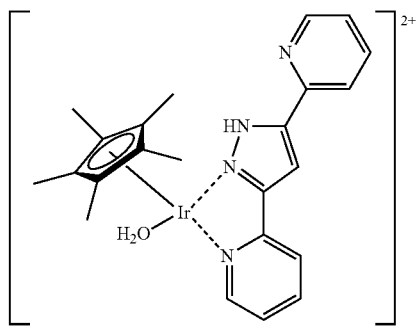
(19)

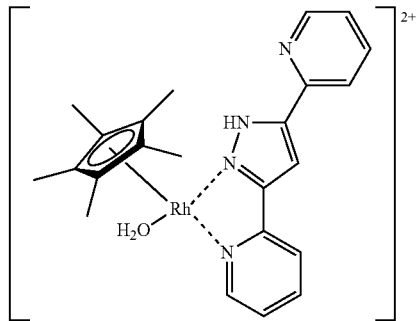
(20)

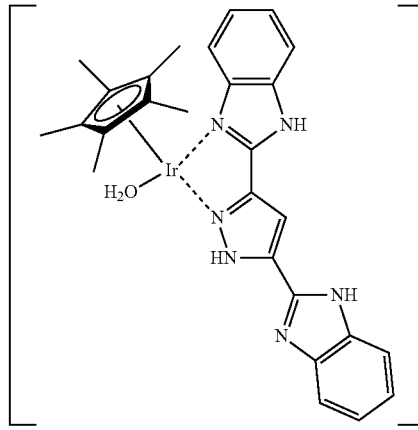
(21)

A method for dehydrogenating at least one of formic acid and a formic acid salt, the method including:
allowing a solution containing at least one of formic acid and a formic acid salt to react in the presence of the catalyst according to any one of [1] to [7].

[9] A method for producing hydrogen, the method including:
allowing a solution containing at least one of formic acid and a formic acid salt to react in the presence of the catalyst according to any one of [1] to [7], to thereby dehydrogenate the at least one of formic acid and a formic acid salt.

The present invention may include the following aspects.

[10] The method according to [8] or [9], wherein the reaction is performed at a concentration of the at least one of formic acid and a formic acid salt of 2 M or more.

[11] The method according to any one of [8], [9], and [10], wherein the reaction is performed at a concentration of the at least one of formic acid and a formic acid salt of 5 M or more.

[12] The method according to any one of [8], [9], [10], and [11], wherein the reaction is performed under a condition of 70° C. or higher.

[13] The method according to any one of [8], [9], and [10] to [12], wherein the reaction is performed under a condition of 80° C. or higher.

[14] The method according to any one of [8], [9], and [10] to [13], wherein the reaction is performed under a condition of 0.2 MPa or higher.

[15] The method according to any one of [8], [9], and [10] to [14], wherein the reaction is performed under a condition of 1 MPa or higher.

Advantageous Effects of Invention

Use of a complex according to the present invention, an isomer or a salt of the complex as a catalyst enables to provide a high-pressure hydrogen gas free of carbon monoxide through dehydrogenation of formic acid or a formic acid salt in a highly efficient, highly energy-efficient, highly selectively, and highly durable manner. Use of a method for dehydrogenating according to the present invention allows hydrogen to be regenerated easily from formic acid or a formic acid salt which is liquid fuel suitable for transportation and storage.

A complex catalyst according to the present invention has extremely higher durability than those of the complex catalysts described in PTLs 12 to 14, and has excellent catalytic performance allowing the catalyst to stably maintain high catalytic performance for a long period of time in a high-concentration formic acid solution under a high temperature reaction condition.

DESCRIPTION OF EMBODIMENTS

Figure 1:
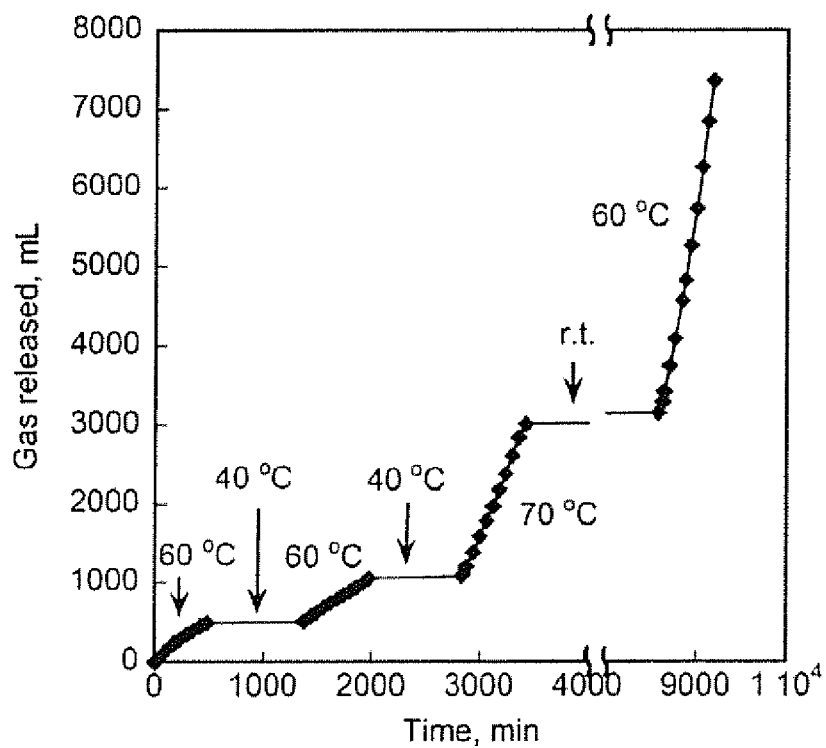
FIG. 1 is a graph illustrating a time-dependent change in an amount of a gas released through dehydrogenation of formic acid by a dehydrogenation reaction of the formic acid using an 8 M aqueous formic acid solution with the complex catalyst (18).

As used herein, the phrase "at least one of formic acid and a formic acid salt" refers to the formic acid alone, the formic acid salt alone, a mixture of the formic acid with the formic acid salt, or a mixture of the formic acid or the formic acid salt with an acid or a base.

In the present invention, a dehydrogenation reaction of at least one of formic acid and a formic acid salt represented by the following scheme allows hydrogen and carbon dioxide to be highly efficiently produced. Upon the reaction, there is a possibility that carbon monoxide and water are by-produced through a decarbonylation reaction of formic acid. However, use of a catalyst for dehydrogenation of formic acid according to the present invention allows only the dehydrogenation reaction of formic acid to proceed in a highly selective and highly efficient manner, to thereby produce a hydrogen gas free of carbon monoxide.

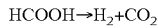

In the complex catalyst represented by the General Formula (1) or (2), examples of transition metals $M^1$ and $M^2$ include iridium, rhodium, ruthenium, cobalt, osmium, nickel, iron, palladium and platinum. Particularly preferable is iridium.

In the complex catalyst represented by the General Formula (1) or (2), substituents $R^1$ to $R^{13}$ each independently are a hydrogen atom, an alkyl group, a hydroxy group (—OH), alkoxy group (—OR), a nitro group, a halogen group, a sulfone group, a carboxylic acid group, an alkylamino group, or a phenyl group, or adjacent R groups may be linked together to form a ring; and $R^1$ to $R^{13}$ may be substituted by one substituent or a plurality of substituents, provided that when $X^i$ (where i denotes 13 to 16) is nitrogen, $R^i$ is absent at a position corresponding to the nitrogen. In particular, the substituents are desirably a hydroxy group (—OH) or an oxyanion group (—O—).

In the complex catalyst represented by the General Formula (1) or (2), at least one of $X^1$ to $X^4$, $X^5$ to $X^8$, and $X^9$ to $X^{12}$ is a nitrogen atom, and all others are a carbon atom. $X^{13}$ to $X^{16}$ are a nitrogen atom or a carbon atom.

In the complex catalyst represented by the General Formula (1) or (2), aromatic anionic ligands or aromatic ligands $L^1$ and $L^2$ are substituted with a hydrogen atom, an alkyl group such as a methyl group, or any substituent. The any substituent may be an aromatic group, a hydroxyl group (—OH), an ester group (—COOR), an amide group (—CONRR'), a halogen (—X), an alkoxy group (—OR), an alkylthio group (—SR), an amino group (—NRR'), a carboxylate group (—COOH), nitro group, or a sulfonate group (—SO$_3$H), which may be the same as or different from each other. Particularly preferable is a pentamethylcyclopentadienyl ligand in which all substituents are methyl groups.

In the complex catalyst represented by any of the Formulae (1) to (12), a ligand $Z^1$ or $Z^2$ may be a water molecule, a hydrogen atom, an alkoxide ion, a hydroxide ion, a halide ion, a carbonate ion, a trifluoromethanesulfonate ion, a sulfate ion, a nitrate ion, a formate ion, or an acetate ion, or may be absent. The alkoxide ion is not particularly limited. Examples thereof include alkoxide ions derived from, for example, methanol, ethanol, n-propyl alcohol, isopropyl alcohol, n-butyl alcohol, sec-butyl alcohol, isobutyl alcohol, or tert-butyl alcohol.

In the complex catalyst represented by any of the Formulae (1) to (12), the ligand $Z^1$ or $Z^2$ may be relatively easy substituted or desorbed depending on the type thereof. As an example, the ligand $Z^1$ or $Z^2$ becomes a water molecule (—OH$_2$) in an acidic aqueous solution or —OH in an alkaline aqueous solution. The ligand easily becomes a hydrogen atom in the presence of a hydrogen gas or a formic acid molecule, becomes an alkoxide ion in an alcoholic solvent, or may undergo photodesorption or thermodesorption. However, the above description is intended to only exemplify possible mechanisms, and the present invention is not limited thereto.

In the complex catalyst represented by any of the Formulae (1) to (12), m and n is a positive integer, 0, or a negative integer.

In the complex catalyst represented by any of the Formulae (1) to (21), a counter ion thereof is not particularly limited. Examples of anions serving as the counter ion include a hexafluorophosphate ion (PF$_6^-$), a tetrafluoroborate ion ($BF_4^-$) a hydroxide ion ($OH^-$), an acetate ion, a carbonate ion, a phosphate ion, a sulfate ion, a nitrate ion, a halide ion (e.g., a fluoride ion ($F^-$) a chloride ion ($Cl^-$) a bromide ion ($Br^-$) and an iodide ion ($I^-$)), a hypohalite ion (e.g., a hypofluorite ion, a hypochlorite ion, a hypobromite ion, and a hypoiodite ion), a halite ion (e.g., a fluorite ion, a chlorite ion, a bromite ion, and an iodide ion), a halate ion (e.g., a fluorate ion, a chlorate ion, a bromate ion, and an iodate ion), a perhalate ion (e.g., a perfluorate ion, a perchlorate ion, a perbromate ion, and a periodate ion), a trifluoromethanesulfonate ion ($OSO_2CF_3^-$), and a tetrakis (pentafluorophenyl)borate ion [$B(C_6F_5)_4^-$]. Examples of cations serving as the counter ion include, but are not limited to, various metal ions, such as a lithium ion, a magnesium ion, a sodium ion, a potassium ion, a calcium ion, a barium ion, a strontium ion, an yttrium ion, a scandium ion, and a lanthanoid ion; and a hydrogen ion. One type of these counter ions may be used alone, or two or more types may be used in combination. However, the above description is intended to only exemplify possible mechanisms, and the present invention is not limited thereto.

Notably, examples of the alkyl group in the present invention include, but are not limited to, a methyl group, an ethyl group, an n-propyl group, an isopropyl group, an n-butyl group, an isobutyl group, a sec-butyl group and a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same can be applied to a group and an atomic group (e.g., an alkoxy group) derived from the alkyl group. Examples of the alcohol and the alkoxide ion include, but are not limited to, alcohols and alkoxide ions derived from the above-described alkyl groups. Moreover, as used herein, the term "halogen" refers to any halogen element. Examples thereof include fluorine, chlorine, bromine, and iodine. In the present invention, in the case where a substituent has an isomer, any isomer may be used unless otherwise restricted. For example, a "propyl group" as simply referred to herein may be an n-propyl group or an isopropyl group. Similarly, a "butyl group" as simply referred to herein may be an n-butyl group, an isobutyl group, a sec-butyl group, or a tert-butyl group. However, the above description is intended to only exemplify possible mechanisms, and the present invention is not limited thereto.

The catalyst according to the present invention is a catalyst containing, as an effective ingredient, a complex represented by any of the General Formulae (1) to (21), tautomers or stereoisomers thereof, or salts thereof, and used for a method for dehydrogenating at least one of formic acid and a formic acid salt (or a method for producing hydrogen) or a method for producing hydrogen. The effective ingredient of the catalyst includes at least one compound selected from the group consisting of a complex represented by any of the Formulae (1) to (21), tautomers thereof, stereoisomers thereof, and salts thereof. For example, one compound or a plurality of compounds serving as the effective ingredient may be used as-is as the complex catalyst according to the present invention, or a mixture of the above-described isomers may be used as the complex catalyst. Other ingredients may be appropriately added (preferably in an amount of less than 10% by mass).

In the complex catalyst according to the present invention, any one of aromatic rings constituting the ligand includes an aromatic heterocyclic 5-membered ring skeleton having 2 or more nitrogen atoms. The ligand significantly improves efficiency of the dehydrogenation reaction of formic acid. For example, a bipyridine complex which contains a bidentate ligand including a 6-membered ring skeleton similar to the complex catalyst represented by the General Formula (1) or (2) exhibits only extremely low catalytic performance in the dehydrogenation reaction of formic acid (see, Comparative Example 1). From the above results, it has been found that it is necessary for one or more of aromatic rings constituting the ligand to include an aromatic heterocyclic 5-membered ring skeleton having 2 or more nitrogen atoms in order to accelerate the dehydrogenation reaction of formic acid.

A method for dehydrogenating formic acid (or a method for producing hydrogen) according to the present invention includes at least one step selected from the group consisting of a step of stirring a solution containing at least one of formic acid and a formic acid salt with a catalyst containing, as the effective ingredient, the complex catalyst, tautomers or stereoisomers thereof, or salts thereof according to the present invention, and a step of heating the solution. Specifically, for example, the complex catalyst according to the present invention is added to solution containing at least one of formic acid and a formic acid salt, and then stirred, optionally with heating. In the case of heating, a temperature is not particularly limited, but is, for example, 0° C. to 300° C., preferably 20° C. to 120° C., more preferably 60° C. to 100° C. A method for collecting hydrogen released is not particularly limited. For example, known methods such as a downward displacement of water method or an upward displacement method may be appropriately used.

In the method for dehydrogenating formic acid (or a method for producing hydrogen) according to the present invention, the formic acid or the formic acid salt can also be dehydrogenated under pressure by using a sealable reaction container. A gas pressure in the reaction container is not particularly limited, but is, for example, 0 MPa to 100 MPa, preferably 1 MPa to 10 MPa. Pressure inside the reaction container is spontaneously increased, which allows high pressure hydrogen gas to be spontaneously supplied without pressurizing by means of external energy.

In the method for dehydrogenating formic acid (or a method for producing hydrogen) according to the present invention, a concentration of the complex catalyst is not particular limited, but depends on, for example, reaction velocity, solubility of the complex in the reaction solution, and economic efficiency. Appropriate concentration of the catalyst is $1 \times 10^{-9}$ M to $1 \times 10^{-1}$ M, preferably $1 \times 10^{-7}$ M to $1 \times 10^{-1}$ M.

In the method for dehydrogenating formic acid (or a method for producing hydrogen) according to the present invention, a ratio of an amount of substance (the number of molecules) of catalyst molecules to that of formic acid molecules is not particularly limited, but, for example, the ratio of the formic acid molecules to the catalyst molecules is 100:1 to 1:100,000,000 at the start of the reaction. Hydrogen can be continuously produced by additionally adding or continuously adding dropwise formic acid molecules during the reaction. As used herein, the term formic molecule includes formic acid and a formic acid salt, which may be used alone or as a mixture thereof. In the case where the mixture is used, it is generally used in a pH range of 1 to 9, preferably 1 to 6, but the formic acid may be dehydrogenated at a pH out of the above range by additionally adding an acid or a base. In the case where the formic acid salt is used alone, examples of a positive ion serving as a counter cation include, but are not limited to, various metal ions such as a lithium ion, a magnesium ion, a sodium ion, a potassium ion, a calcium ion, a barium ion, a strontium ion, an yttrium ion, a scandium ion, or a lanthanoid ion, an ammonium ion, tetramethyl ammonium, and tetraethyl ammonium. Although these counter ions may be used alone or two or more counter ions may be used in combination.

The catalyst, a tautomer or stereoisomer thereof, or a salt thereof according to the present invention can be used as a catalyst for dehydrogenation of formic acid in, for example, a formic acid fuel cell. In the case where the catalyst is used in the fuel cell, for example, the cell only has to contain therein the catalyst for dehydrogenation of formic acid according to the present invention and include a mechanism for generating hydrogen by dehydrogenating formic acid according to the above described method. A specific configuration of the fuel cell is not particularly limited, and, for example, a configuration of a known fuel cell can be appropriately applied thereto. Furthermore, an application of the catalyst for dehydrogenation of formic acid according to the present invention is not limited to those mentioned above, and, for example, the catalyst for dehydrogenation of formic acid according to the present invention can be used in every technical field in which hydrogen ($H_2$) is needed to be supplied.

In the method for dehydrogenating formic acid according to the present invention, a reaction solvent to be used is not particularly limited. For example, the solvent may be water or an organic solvent, and one solvent may be used alone or two or more solvents may be used in combination. In the case where the complex catalyst according to the present invention is soluble in water, water is preferably used from the viewpoint of simplicity and convenience. The organic solvent is not particularly limited, but a highly polar solvent is preferable from the viewpoint of solubility of the catalyst. Examples thereof include nitriles such as acetonitrile, propionitrile, butyronitrile, or benzonitrile; primary alcohols such as methanol, ethanol, n-preppy alcohol, or n-butyl alcohol; secondary alcohols such as isopropyl alcohol or s-butyl alcohol; tertiary alcohols such as t-butyl alcohol; polyhydric alcohols such as ethylene glycol or propylene glycol; ethers such as tetrahydrofuran, dioxane, dimethoxyethane, or diethyl ether; amides such as dimethylformamide or dimethylacetamide; sulfoxides such as dimethyl sulfoxide; and esters such as ethyl acetate. Furthermore, formic acid as a raw material may be in the form of a solution or a salt.

EXAMPLES

Hereinafter, examples of the present invention will be described in more detail. However, the present invention is not limited to the following examples.

Example 1

[Catalyst Synthesis]
(Synthesis of Sulfate of Complex Catalyst Represented by General Formula (1) or (2))

[Cp*Ir(H$_2$O)$_3$]SO$_4$ and a ligand corresponding to it in an equal amount were dissolved into water, followed by stirring at room temperature under an argon stream for 12 hours. The resultant reaction liquid was filtered. The resultant filtrate was concentrated under reduced pressure. The resultant product was dried at 50° C. under reduced pressure for 12 hours, to thereby the intended product.

The spectral data of the resultant complex catalysts are presented below.

Example 1-1

The spectral data of the compound represented by the following Formula (22) is presented below.

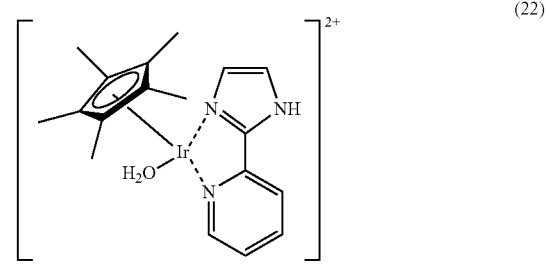

(22)

$^1$H NMR (400 MHz, D$_2$O): δ=8.95 (dt, J=5.6, 1.1 Hz, 1H), 8.22-8.06 (m, 2H), 7.65 (ddd, J=7.4, 5.6, 1.6 Hz, 1H), 7.56 (dd, J=19.2, 1.6 Hz, 2H), 1.63 (s, 15H); IR (KBr): 1622, 1174, 1203, 1110, 791 cm$^{-1}$; UV/Vis: λ$_{max}$ 272 nm; ESI-MS (m/z): [M-SO$_4$—H$_2$O—H]$^+$. found, 472.1; Elemental analysis calcd. for C$_{18}$H$_{24}$IrN$_3$O$_5$S+H$_2$O: C, 34.83; H, 4.22; N, 6.77. Found: C, 31.74; H, 4.38; N, 6.52.

Example 1-2

The spectral data of the compound represented by the following Formula (23) is presented below.

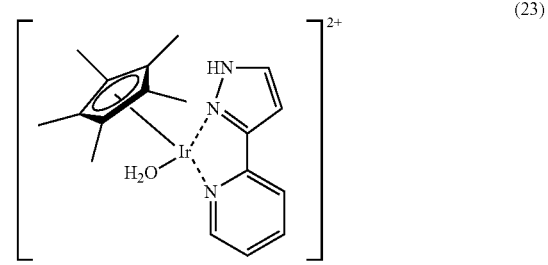

(23)

$^1$H NMR (400 MHz, D$_2$O): δ=8.91 (d, J=5.7 Hz, 1H), 8.19-8.07 (m, 2H), 8.04 (d, J=2.9 Hz, 1H), 7.63 (ddd, J=7.3, 5.7, 1.9 Hz, 1H), 7.09 (d, J=2.9 Hz, 1H), 1.63 (s, 15H); IR (KBr): 1615, 1458, 1192, 1113, 782 cm$^{-1}$; UV/Vis: λ$_{max}$ 300 nm (shoulder peak); ESI-MS (m/z): [M-SO$_4$—H$_2$O—H]$^+$. found, 472.1; Elemental analysis calcd. for C$_{18}$H$_{24}$IrN$_3$O$_5$S+H$_2$O: C, 34.83; H, 4.22; N, 6.77. Found: C, 35.22; H, 4.39; N, 6.85.

Example 1-3

The spectral data of the compound represented by the following Formula (24) is presented below.

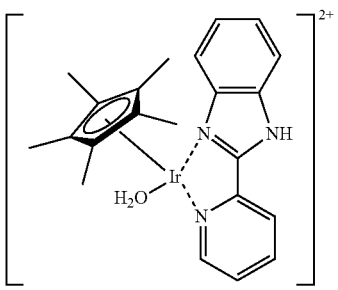

(24)

$^1$H NMR (400 MHz, D$_2$O): δ=9.11 (d, J=5.4 Hz, 1H), 8.37 (d, J=7.8 Hz, 1H), 8.30 (t, J=7.9 Hz, 1H), 7.91-7.75 (m, 3H), 7.59-7.52 (m, 2H), 1.67 (s, 15H); IR (KBr): 1625, 1459, 1118, 1027, 764 cm$^{-1}$; UV/Vis: λ$_{max}$ 330 nm; ESI-MS (m/z): [M-SO$_4$—H$_2$O—H]$^+$. found, 522.1; Elemental analysis calcd. for C$_{22}$H$_{26}$IrN$_3$O$_5$S+H$_2$O: C, 39.39; H, 4.21; N, 6.26. Found: C, 39.52; H, 4.19; N, 6.00.

Example 1-4

The spectral data of the compound represented by the following Formula (25) is presented below.

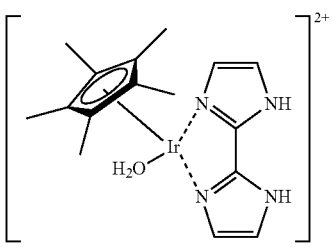

(25)

$^1$H NMR (400 MHz, D$_2$O): δ=7.52 (t, J=1.6 Hz, 2H), 7.41 (t, J=1.6 Hz, 2H), 1.67 (s, 15H); UV/Vis: λ$_{max}$ 289 nm; ESI-MS (m/z): [M-SO$_4$—H$_2$O—H]$^+$. found, 461.59.

Example 1-5

The spectral data of the compound represented by the following Formula (26) is presented below.

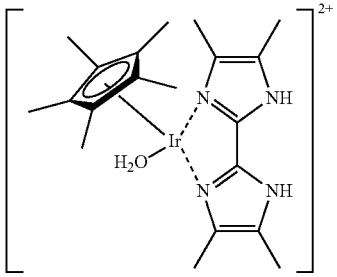

(26)

$^1$H NMR (400 MHz, D$_2$O): δ=2.18 (d, J=1.4 Hz, 6H), 2.27 (d, J=1.4 Hz, 6H), 1.57 (d, J=1.5 Hz, 15H); IR (KBr): 1593, 1193, 1114, 799 cm$^{-1}$; UV/Vis: λ$_{max}$ 314 nm; ESI-MS(m/z): [M-SO$_4$—H$_2$O—H]$^+$. found, 517.1; Elemental analysis calcd. for C$_{20}$H$_{31}$IrN$_4$O$_5$S: C, 38.02; H, 4.95; N, 8.87. Found: C, 38.07; H, 4.78; N, 8.63.

Example 1-6

The spectral data of the compound represented by the following Formula (27) is presented below.

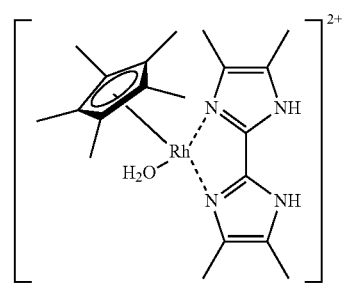

(27)

$^1$H NMR (400 MHz, D$_2$O): δ=2.31 (s, 6H), 2.18 (s, 6H), 1.59 (s, 15H); IR (KBr): 1622, 1413, 1140 cm$^{-1}$; UV/Vis: λ$_{max}$ 317 nm; ESI-MS (m/z): [M-SO$_4$—H$_2$O—H]$^+$. found, 427.1; Elemental analysis calcd. for C$_{20}$H$_{31}$RhN$_4$O$_6$S+ 1.3H$_2$O: C, 42.6; H, 5.65; N, 9.94. Found: C, 42.8; H, 5.68; N, 9.65.

Example 1-7

The spectral data of the compound represented by the Formula (15) is presented below.

$^1$H NMR (D$_2$O, 400 MHz): 7.38 (s, 1H), 7.19 (s, 1H), 6.01 (s, 1H), 1.63 (s, 15H). $^1$H NMR (DMSO-d$_6$, 400 MHz): 10.89 (s, 1H), 7.86 (s, 1H), 7.57 (s, 1H), 6.12 (s, 1H), 1.69 (s, 15H); ESI-MS (+): m/z 505.2 [M-H$_2$O—H]$^+$.

Example 1-8

The spectral data of the compound represented by the Formula (16) is presented below.

$^1$H NMR (D$_2$O, 400 MHz): 8.68 (d, J=3.2 Hz, 1H), 8.37 (d, J=3.2 Hz, 1H), 8.00 (t, J=1.0 Hz, 1H), 7.42 (d, J=8 Hz, 1H), 6.98 (t, J=3.2 Hz, 2H), 1.69 (s, 15H); $^{13}$C NMR (D$_2$O, 125 MHz): δ=164.09, 146.86, 115.24, 143.88, 132.22, 112.45, 110.61, 101.99, 89.77, 8.97. ESI-MS (+): m/z 488.1 [M-H$_2$O—H]$^+$.

Example 1-9

The spectral data of the compound represented by the Formula (17) is presented below.

$^1$H NMR (DMSO-d$_6$, 400 MHz): 11.38 (s, 1H), 8.65 (s, 1H), 8.45 (s, 1H), 7.03 (s, 1H), 5.29 (s, 1H), 1.73 (s, 15H); $^{13}$C NMR (DMSO-d$_6$, 125 MHz): 169.56, 168.59, 145.18, 133.44, 111.97, 96.26, 87.89, 8.83; ESI-MS: 505.1 [M-H$_2$O—H]$^+$. Anal. Calc. for C$_{17}$H$_{23}$IrN$_4$O$_7$S.0.5H$_2$O: C, 32.4.8, H, 3.85, N, 8.91. Found: C, 32.62, H, 3.63, N, 8.66.

Example 1-10

The spectral data of the compound represented by the Formula (18) is to presented below.

$^1$H NMR (D$_2$O, 400 MHz): δ=7.38 (s, 1H), 7.19 (s, 1H), 6.01 (s, 1H), 1.63 (s, 15H). $^1$H NMR (d$^6$-DMSO, 400 MHz): 10.89 (s, 1H), 7.86 (s, 1H), 7.57 (s, 1H), 6.12 (s, 1H), 1.69 (s, 15H). $^{13}$C NMR (d$^6$-DMSO, 125 MHz): δ=168.71, 157.91, 127.47, 123.18, 95.95, 87.73, 84.72, 55.90, 8.99. ESI-MS (+): m/z 505.2 [M-H$_2$O—H]$^+$.

[Example 2] Dehydrogenation Reaction of Formic Acid

A solution of the complex catalyst represented by the General Formula (1) or (2) in water was degassed. Thus prepared catalyst solution was added to a 1 M degassed solution of formic acid in water (10 mL), followed by stirring with heating. An amount of gas released was measured by means of a gas meter (Shinagawa W-NK-05). A gas component released was measured by means of a gas chromatography GL SCIENCES (GC390), hydrogen was measured by means of a thermal conductivity detector (TCD), and carbon dioxide and carbon monoxide were measured by means of a mechanizer and a hydrogen flame ionization detector (FID). As a result, it was found that hydrogen and carbon dioxide were released in a ratio of 1:1, and that carbon monoxide was not able to be detected (equal to or lower than the detection threshold of 10 ppm). From the reaction results presented in Table 1, all catalysts including a ligand containing a 5-membered ring, which were according to the present invention, exhibited a high catalytic activity. As described in NPL 18, in the dehydrogenation reaction of formic acid, it has been found that a catalyst is activated by the electron-donating action of a substituent on a ligand in the catalyst. Based on this finding, the catalyst represented by the General Formula (26), which was obtained by introducing four methyl groups to the catalyst represented by the General Formula (25), exhibited a turnover frequency (TOF: the number of substrate (i.e., formic acid) molecules on which the catalyst acts per 1 molecule of the catalyst per 1 hour) 1.75 times higher than that of the catalyst represented by the General Formula (25). Further, when a strong electron-donating hydroxyl group was introduced, the complex represented by the General Formula (15) in which the hydroxyl group had been substituted exhibited the TOF 5 times or more higher than that of the unsubstituted complex represented by the General Formula (22).

TABLE 1

Dehydrogenation reaction of formic acid using complex catalyst

| Catalyst (Concentration/mM) | Concentration of formic acid (M) | Time (h) | Temperature (° C.) | TOF (h$^{-1}$) | Turnover number of catalyst | Conversion rate (%) |
|---|---|---|---|---|---|---|
| (22)/0.5 | 1 | 4 | 60 | 810 | 1,970 | 98 |
| (23)/0.5 | 1 | 7 | 60 | 400 | 2,000 | >99 |
| (24)/0.5 | 1 | 6 | 60 | 570 | 2,000 | >99 |
| (25)/0.1 | 1 | 5 | 60 | 3,980 | 10,000 | 100 |
| (26)/0.1 | 1 | 2 | 60 | 7,020 | 10,000 | 100 |
| (27)/0.5 | 2 | 8 | 60 | 250 | 1,020 | 26 |
| (26)/0.1 | 1 | 0.5 | 80 | 34,000 | 10,000 | 100 |
| (15)/0.1 | 1 | 5 | 60 | 4,290 | 10,000 | 100 |
| (16)/0.1 | 1 | 7 | 60 | 2,740 | 10,000 | 100 |
| (17)/0.1 | 1 | 3.5 | 60 | 5,150 | 10,000 | 100 |
| (18)/0.1 | 1 | 7 | 60 | 7,050 | 10,000 | 100 |
| (19)/0.1 | 1 | 2.5 | 60 | 6,300 | 10,000 | 100 |
| (20)/0.1 | 1 | 3 | 60 | 290 | — | — |
| (21)/0.1 | 1 | 3 | 60 | 6,620 | 10,000 | 100 |

[Example 3] Dehydrogenation Reaction of Formic Acid

A solution of the complex catalyst represented by the General Formula (18) in water was degassed. Thus prepared catalyst solution (1 μmol) was added to an 80% degassed solution of formic acid in water (10 mL), followed by stirring with heating. The catalytic reaction proceeded for 150 hours or longer. After the reaction, the formic acid was completely decomposed. A time-dependent change in an amount of a gas released is illustrated in FIG. 1. This complex catalyst was able to exhibit stable catalytic performance without deteriorating for 1 week or longer even in a high-concentration formic acid solution.

Example 4

Figure 2:
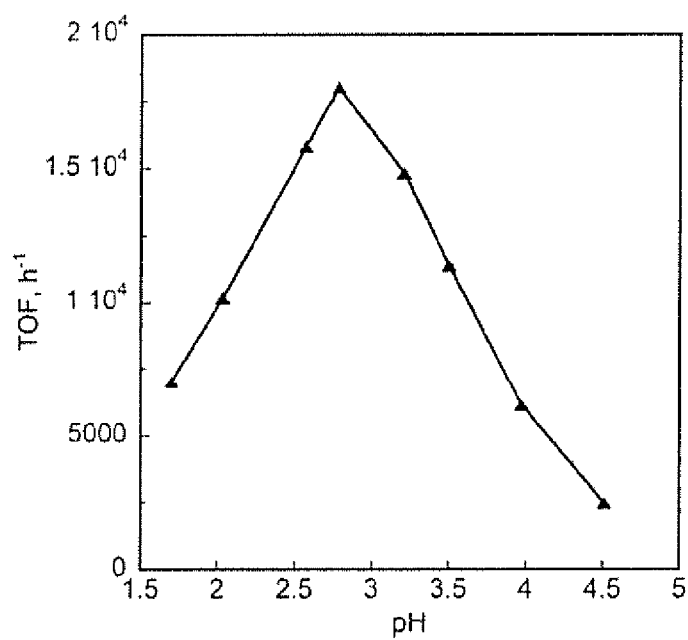
FIG. 2 is a graph illustrating a pH-dependent change in reaction velocity of a dehydrogenation reaction of formic acid with the complex catalyst (18).

A solution of the complex catalyst represented by the General Formula (18) in water was degassed. Thus prepared catalyst solution (100 μL, 1 μmol) was added to a 1 M degassed solution of formic acid/sodium formate (100/0 to 0/100) in water (10 mL) of which pH had been adjusted, followed by stirring at 60° C. A pH-dependent change in reaction velocity is illustrated in FIG. 2.

Example 5

Figure 3:
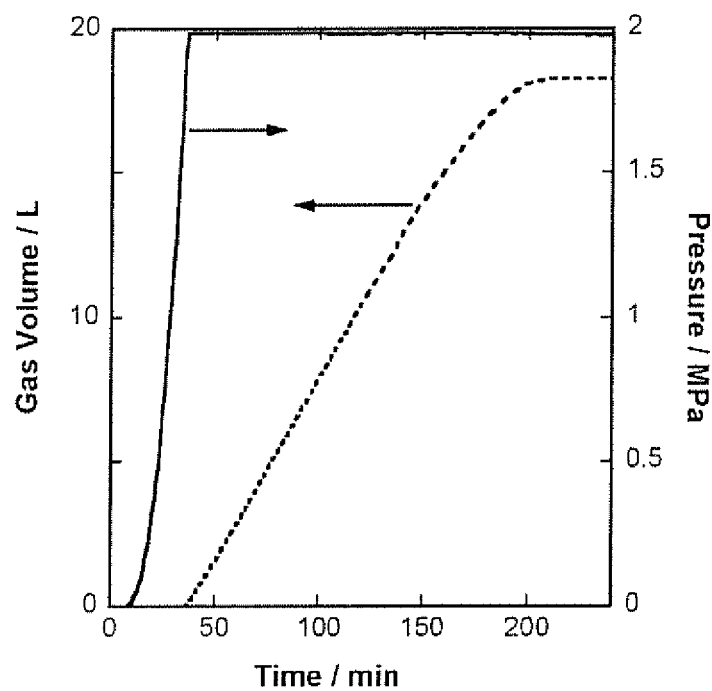
FIG. 3 is a graph illustrating a time-dependent change in volume and pressure of a gas released from an 8 M aqueous formic acid solution (50 mL) with the mononuclear catalyst (18) in a sealed glass autoclave with a back pressure valve pressure of 2 MPa at a reaction temperature of 80° C.
Figure 4:
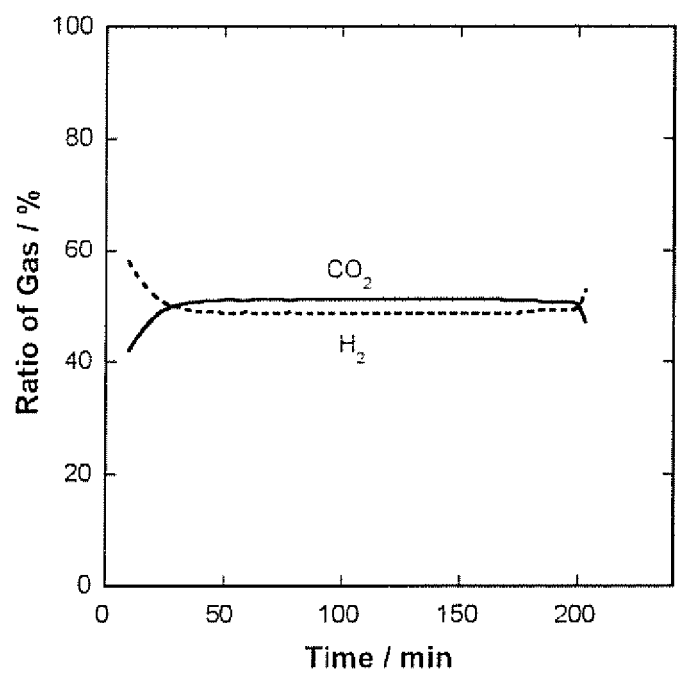
FIG. 4 is a graph illustrating a time-dependent change in ratios of carbon dioxide and a hydrogen gas released from an 8 M aqueous formic acid solution (50 mL) with the mononuclear catalyst (18) in a sealed glass autoclave with a back pressure valve pressure of 2 MPa at a reaction temperature of 80° C.

An 8 M degassed solution of formic acid in water (50 mL) containing the complex catalyst represented by the General Formula (18) (5 μmol) was placed into a glass autoclave. The reaction container was stirred with heating at 80° C., and amounts and ratios of gases released from a back pressure valve at 2 MPa were measured (FIGS. 3 and 4). As a result, a turnover efficiency of the catalyst was extremely high, i.e., 34,000 times per 1 hour. It was confirmed that hydrogen and carbon dioxide were released in a ratio of approximately 1:1 and that 99% or more of the formic acid was decomposed after the reaction. These results indicate that hydrogen is released without deteriorating the complex catalyst even under severe reaction conditions, that is, in a high-concentration aqueous formic acid solution, at a high temperature of 80° C. and high pressure of 2 MPa.

Comparative Example 1

In a dehydrogenation reaction of formic acid using the unsubstituted bipyridine complex catalyst represented by the General Formula (28) (1 M aqueous formic acid solution, reaction temperature: 60° C.), the TOF was 30. The catalyst according to the present invention exhibited significantly higher catalytic activity than that value under the same reaction conditions. The complex represented by the General Formula (29), which was an active form of the complex represented by the General Formula (28) obtained by introducing hydroxyl groups to a ligand thereof, had the TOF of 1,800. Therefore, according to the present invention, it has been found that a catalyst exhibiting excellent catalytic performance can be designed only by including a 5-membered ring skeleton on a ligand thereof. In fact, the complex catalyst represented by the General Formula (18) in which a hydroxyl group had been introduced to a ligand thereof exhibited the highest catalytic performance.

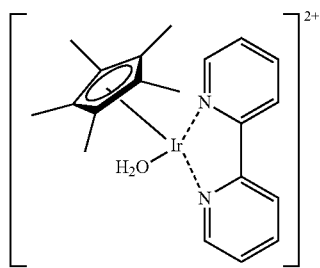

(28)

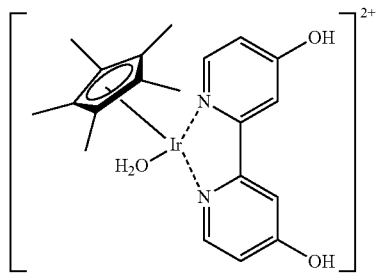

(29)

Comparative Example 21

The catalyst for dehydrogenation of formic acid represented by the General Formula (30) where R=H or OH described in PTLs 12 and 13 exhibits extremely high reaction velocity under the optimal reaction conditions, that is, in a formic acid solution which has a concentration of 1 M or less and of which pH has been adjusted to 3.5, and at a reaction temperature of 70° C. or less. However, the catalytic performance is significantly low under conditions other than the above-described optimal reaction conditions. The conversion rate of formic acid after reaction is low (50%). On the other hand, under severe reaction conditions, that is, in a formic acid solution having a concentration of 2 M or more and/or at a temperature of 80° C. or higher, the catalytic performance was significantly deteriorated within 1 hour.

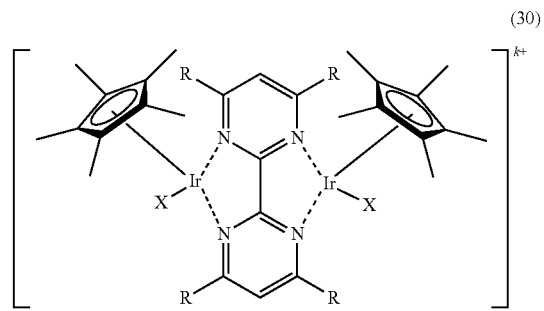

(30)

INDUSTRIAL APPLICABILITY

In the present invention, a metal catalyst which contains a bidentate ligand including an aromatic heterocyclic 5-membered ring having 2 or more nitrogen atoms exhibited extremely high catalytic activity and extremely high durability in production of hydrogen through dehydrogenation of formic acid. Therefore, use of the metal catalyst which contains a bidentate ligand including an aromatic heterocyclic 5-membered ring having 2 or more nitrogen atoms according to the present invention enables to easily and conveniently produce hydrogen from formic acid which can be easily transported and stored. In particular, high pressure hydrogen can be produced through a selective dehydrogenation reaction of formic acid without by-producing carbon monoxide. Therefore, hydrogen can be supplied as fuel for fuel cells without using a gas reformer.

The invention claimed is:
1. A catalyst and its isomer including counter-ion configured for use in a dehydrogenation reaction of formic acid and/or a formic acid salt, the catalyst comprising:
(i) a complex represented by a structure represented by any selected from the group consisting of the following Formulae (7) to (12):

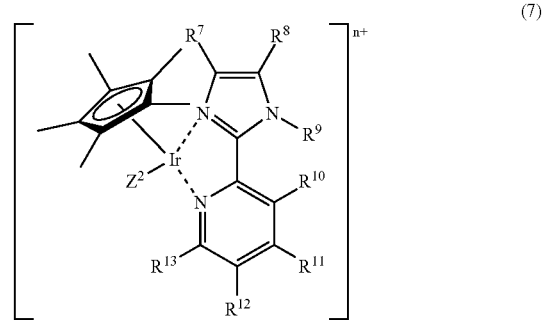

(7)

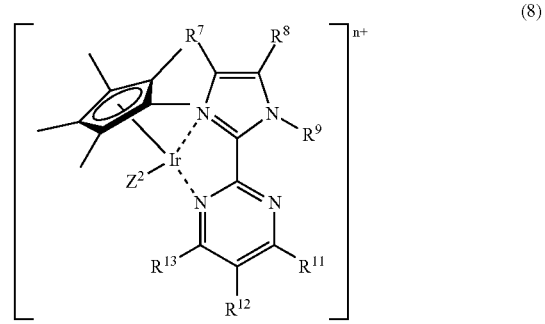

(8)

-continued

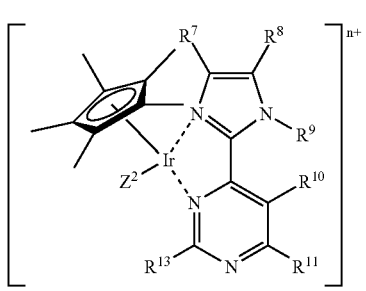
(9)

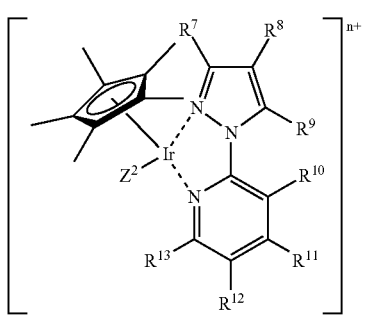
(10)

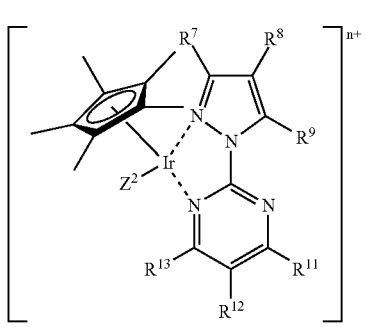
(11)

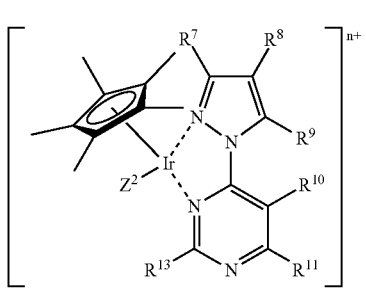
(12)

where
- $X^9$ to $X^{16}$ each independently denote nitrogen or carbon, provided that at least one of $X^9$ to $X^{12}$ is nitrogen;
- $R^7$ to $R^{13}$ each independently denote a hydrogen atom, an alkyl group, a hydroxy group (—OH), an alkoxy group (—OR), a nitro group, a halogen group, a sulfone group, a carboxylic acid group, an alkylamino group, or a phenyl group, or adjacent R groups may be linked together to form a ring; and $R^1$ to $R^{13}$ may be substituted by one substituent or a plurality of substituents, provided that when $X^i$ (where i denotes 13 to 16) is nitrogen, $R^i$ where i denotes 7-13) is absent at a position corresponding to the nitrogen;
- $Z^2$ denotes any ligand or is absent; and
- n denotes a positive integer, 0, or a negative integer.

2. The catalyst configured for use in a dehydrogenation reaction of at least one of formic acid and a formic acid salt according to claim 1, wherein any ligand in $Z^2$ denotes a water molecule, a hydrogen atom, an alkoxide ion, a hydroxide ion, a halide ion, a carbonate ion, a trifluoromethanesulfonate ion, a sulfate ion, a nitrate ion, a formate ion, or an acetate ion, or is absent.

3. The catalyst configured for use in a dehydrogenation reaction of at least one of formic acid and a formic acid salt according to claim 1, wherein the complex has a structure represented by any selected from the group consisting of the following Formulae (13) to (18):

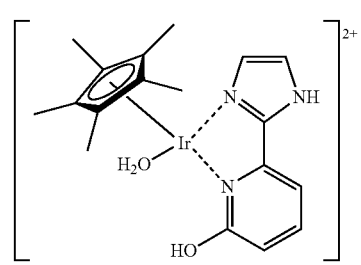
(13)

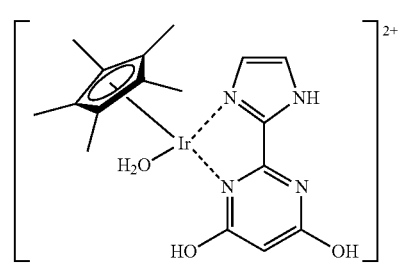
(14)

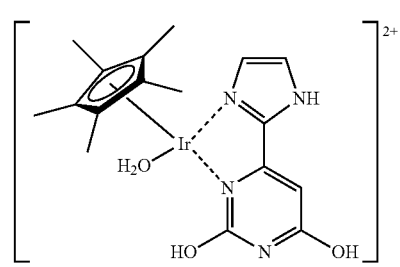
(15)

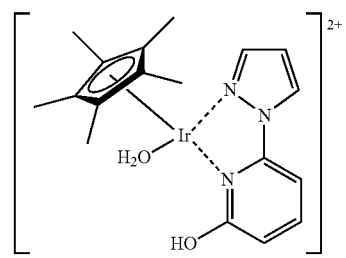
(16)

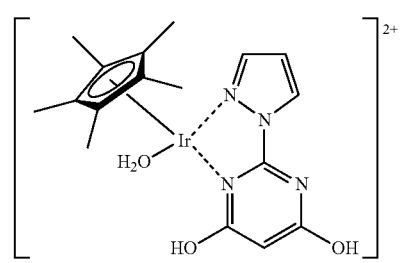
(17)

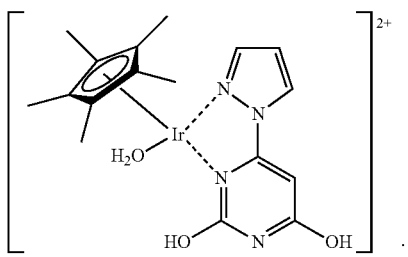

(18)

4. A catalyst and its isomer including counter-ion configured for use in a dehydrogenation reaction of formic acid and/or a formic acid salt, the catalyst comprising:
(i) a complex represented by the following Formula (1) which comprises a bidentate ligand comprising two aromatic heterocyclic 5-membered rings each having 2 or more nitrogen atoms,

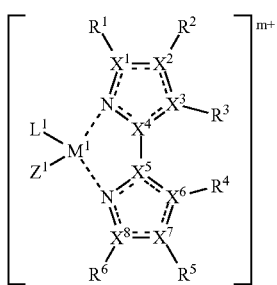

(1)

where
$M^1$ denotes iridium;
$X^1$ and $X^8$ each denote nitrogen and $X^2$, $X^3$, $X^4$, $X^5$, $X^6$, and $X^7$ each denote carbon;
$R^1$ to $R^6$ each independently denote a hydrogen atom, an alkyl group, a hydroxy group (—OH), an alkoxy group (—OR), a nitro group, a halogen group, a sulfone group, a carboxylic acid group, an alkylamino group, or a phenyl group, or adjacent R groups may be linked together to form a ring; and $R^1$ to $R^6$ may be substituted by one substituent or a plurality of substituents, provided that when $X^i$ (where i denotes 13 to 16) is nitrogen, $R^i$ (where i denotes 7 to 13) is absent at a position corresponding to the nitrogen;
$L^1$ denotes an aromatic anionic ligand or an aromatic ligand, and may be substituted by one substituent or a plurality of substituents;
$Z^1$ denotes any ligand or is absent; and
m denotes a positive integer, 0, or a negative integer.

5. A catalyst configured for use in a dehydrogenation reaction of at least one of formic acid and a formic acid salt, wherein the complex has a structure represented by any selected from the group consisting of the following Formulae (19) to (20):

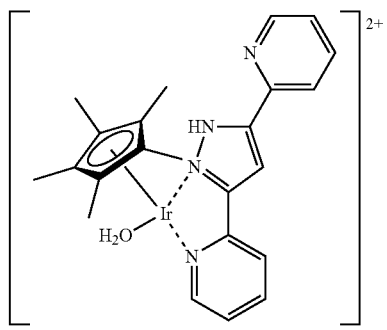

(19)

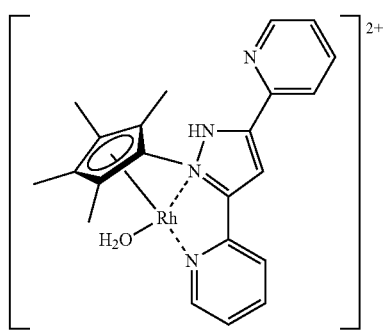

(20)

* * * * *